US010120112B2

(12) United States Patent
Tabirian et al.

(10) Patent No.: US 10,120,112 B2
(45) Date of Patent: Nov. 6, 2018

(54) DIFFRACTIVE WAVEPLATE LENSES FOR CORRECTING ABERRATIONS AND POLARIZATION-INDEPENDENT FUNCTIONALITY

(71) Applicants: Nelson V. Tabirian, Winter Park, FL (US); David E. Roberts, Apopka, FL (US); Diane M. Steeves, Franklin, MA (US); Brian R. Kimball, Shrewsbury, MA (US)

(72) Inventors: Nelson V. Tabirian, Winter Park, FL (US); David E. Roberts, Apopka, FL (US); Diane M. Steeves, Franklin, MA (US); Brian R. Kimball, Shrewsbury, MA (US)

(73) Assignees: Beam Engineering for Advanced Measurements Co., Orlando, FL (US); The United States of America as Represented by the Secretary of the Army, Washington, DC (US)

( * ) Notice: Subject to any disclaimer, the term of this patent is extended or adjusted under 35 U.S.C. 154(b) by 27 days.

(21) Appl. No.: 14/688,256

(22) Filed: Apr. 16, 2015

(65) Prior Publication Data
US 2016/0047955 A1 Feb. 18, 2016
US 2018/0039003 A9 Feb. 8, 2018

Related U.S. Application Data

(63) Continuation-in-part of application No. 13/916,627, filed on Jun. 13, 2013, now abandoned, which is a
(Continued)

(51) Int. Cl.
*G02B 5/18* (2006.01)
*G02B 5/30* (2006.01)
*G02B 27/42* (2006.01)

(52) U.S. Cl.
CPC .......... *G02B 5/1833* (2013.01); *G02B 5/3083* (2013.01); *G02B 27/4211* (2013.01); *G02B 27/4216* (2013.01)

(58) Field of Classification Search
CPC .... G02B 5/1833; G02B 3/0081; G02B 5/001; G02B 5/1828; G02B 5/3083; G02B 6/024;
(Continued)

(56) References Cited

U.S. PATENT DOCUMENTS 2,435,616 A 2/1948 Vittum
3,721,486 A 3/1973 Bramley
(Continued)

FOREIGN PATENT DOCUMENTS

EP 1970734 9/2008
EP 2088456 12/2009
(Continued)

OTHER PUBLICATIONS

M. Honma, et. al., "Liquid-Crystal Fresnel Zone Plate Fabricated by Microrubbing," Japanese Journal of Applied Physics, vol. 44, No. 1A, 2005, pp. 287-290.*
(Continued)

*Primary Examiner* — Bumsuk Won
*Assistant Examiner* — Wen Huang
(74) *Attorney, Agent, or Firm* — Brian S. Steinberger; Law Offices of Brian S. Steinberger, P.A.

(57) ABSTRACT

Diffractive waveplate lenses, devices, systems and methods of fabricating and manufacturing lenses for correcting spherical and chromatic aberrations of diffractive waveplate lenses and refractive lenses, by using nonlinear patterning of anisotropy axis of birefringent layers comprising the dif-
(Continued)

fractive waveplate lenses, and their combinations and for obtaining polarization-independent functionality of diffractive waveplate lenses.

14 Claims, 14 Drawing Sheets

Related U.S. Application Data continuation of application No. 12/697,083, filed on Jan. 29, 2010, now abandoned.

(60) Provisional application No. 61/980,062, filed on Apr. 16, 2014.

(58) Field of Classification Search
CPC ............... G02B 6/3534; G02B 6/3592; G02B 27/4205; G02B 27/4211; G02B 27/4216; G02B 27/4261; A61F 2/1654; G02C 7/022; G02C 7/061; G02C 7/086; G02C 7/12; G02C 7/10; G02C 2202/16
USPC .................................................. 359/489.07
See application file for complete search history.

(56) References Cited

U.S. PATENT DOCUMENTS

| | | | |
|---|---|---|---|
| 3,897,136 A | 7/1975 | Bryngdahl | |
| 4,160,598 A | 7/1979 | Firester et al. | |
| 4,301,023 A | 11/1981 | Schuberth | |
| 4,698,816 A | 10/1987 | Chun | |
| 4,956,141 A | 9/1990 | Allen | |
| 4,983,332 A | 1/1991 | Hahn | |
| 5,032,009 A | 7/1991 | Gibbons | |
| 5,042,950 A | 8/1991 | Salmon, Jr. | |
| 5,047,847 A | 9/1991 | Toda | |
| 5,100,231 A | 3/1992 | Sasnett et al. | |
| 5,142,411 A | 8/1992 | Fiala | |
| 5,150,234 A | 9/1992 | Takahashi | |
| 5,218,610 A | 6/1993 | Dixon | |
| 5,325,218 A | 6/1994 | Willett | |
| 5,446,596 A | 8/1995 | Mostrorocco | |
| 5,619,325 A | 4/1997 | Yoshida | |
| 5,621,525 A | 4/1997 | Vogeler et al. | |
| 5,712,721 A | 1/1998 | Large | |
| 5,895,422 A | 4/1999 | Hauber | |
| 5,903,330 A | 5/1999 | Funschilling | |
| 5,989,758 A | 11/1999 | Komatsu | |
| 6,091,471 A | 7/2000 | Kim | |
| 6,107,617 A | 8/2000 | Love et al. | |
| 6,139,147 A | 10/2000 | Zhang | |
| 6,170,952 B1 * | 1/2001 | La Haye | C08G 18/758 351/159.41 |
| 6,219,185 B1 | 4/2001 | Hyde | |
| 6,320,663 B1 | 11/2001 | Ershov | |
| 6,452,145 B1 | 9/2002 | Graves et al. | |
| 6,551,531 B1 | 4/2003 | Ford | |
| 6,678,042 B2 | 1/2004 | Tabirian et al. | |
| 6,728,049 B1 | 4/2004 | Tabirian et al. | |
| 6,792,028 B2 | 9/2004 | Cook | |
| 7,048,619 B2 | 5/2006 | Park | |
| 7,094,304 B2 | 8/2006 | Nystrom | |
| 7,095,772 B1 | 8/2006 | Delfyett et al. | |
| 7,196,758 B2 | 3/2007 | Crawford | |
| 7,319,566 B2 | 1/2008 | Prince | |
| 7,324,286 B1 | 1/2008 | Glebov | |
| 7,450,213 B2 | 11/2008 | Kim et al. | |
| 7,764,426 B2 | 7/2010 | Lipson | |
| 8,045,130 B2 | 10/2011 | Son | |
| 8,077,388 B2 | 12/2011 | Gerton | |
| 8,264,623 B2 | 9/2012 | Marrucci | |
| 8,520,170 B2 | 8/2013 | Escuti | |
| 8,643,822 B2 | 2/2014 | Tan et al. | |
| 8,982,313 B2 | 3/2015 | Escuti et al. | |
| 9,541,772 B2 | 1/2017 | De Sio et al. | |
| 9,557,456 B2 | 1/2017 | Tabirian et al. | |
| 9,592,116 B2 | 3/2017 | De Sio et al. | |
| 9,617,205 B2 | 4/2017 | Tabirian et al. | |
| 9,658,512 B2 | 5/2017 | Tabirian et al. | |
| 9,715,048 B2 | 7/2017 | Tabirian et al. | |
| 9,753,193 B2 | 9/2017 | Tabirian et al. | |
| 9,976,911 B1 | 5/2018 | Tabirian et al. | |
| 9,983,479 B2 | 5/2018 | Tabirian et al. | |
| 10,031,424 B2 | 7/2018 | Tabirian et al. | |
| 10,036,886 B2 | 7/2018 | Tabirian et al. | |
| 2001/0002895 A1 | 6/2001 | Kawano | |
| 2001/0018612 A1 | 8/2001 | Carson et al. | |
| 2001/0030720 A1 | 10/2001 | Ichihashi | |
| 2002/0027624 A1 | 3/2002 | Seiberle | |
| 2002/0097361 A1 | 7/2002 | Ham | |
| 2002/0167639 A1 | 11/2002 | Coates | |
| 2003/0072896 A1 | 4/2003 | Kwok | |
| 2003/0137620 A1 | 7/2003 | Wang | |
| 2003/0152712 A1 | 8/2003 | Motomura | |
| 2003/0206288 A1 | 11/2003 | Tabirian et al. | |
| 2003/0214700 A1 | 11/2003 | Sidorin | |
| 2004/0051846 A1 * | 3/2004 | Blum | G02C 7/022 351/159.41 |
| 2004/0105059 A1 | 6/2004 | Ohyama | |
| 2004/0165126 A1 | 8/2004 | Ooi et al. | |
| 2005/0030457 A1 | 2/2005 | Kuan et al. | |
| 2005/0110942 A1 | 5/2005 | Ide | |
| 2005/0219696 A1 | 10/2005 | Albert et al. | |
| 2005/0271325 A1 | 12/2005 | Anderson et al. | |
| 2005/0280171 A1 * | 12/2005 | Chen | B29C 33/3842 264/2.5 |
| 2006/0008649 A1 | 1/2006 | Shinichiro | |
| 2006/0055883 A1 | 3/2006 | Morris | |
| 2006/0221449 A1 | 10/2006 | Glebov et al. | |
| 2006/0222783 A1 | 10/2006 | Hayashi | |
| 2007/0032866 A1 | 2/2007 | Portney | |
| 2007/0115551 A1 | 5/2007 | Spilman | |
| 2007/0122573 A1 | 5/2007 | Yasuike | |
| 2007/0132930 A1 | 6/2007 | Ryu et al. | |
| 2007/0247586 A1 | 10/2007 | Tabirian | |
| 2007/0258677 A1 | 11/2007 | Chigrinov | |
| 2008/0226844 A1 | 9/2008 | Shemo | |
| 2008/0278675 A1 | 11/2008 | Escuti | |
| 2009/0002588 A1 | 1/2009 | Lee et al. | |
| 2009/0052838 A1 | 2/2009 | McDowall | |
| 2009/0073331 A1 | 3/2009 | Shi | |
| 2009/0122402 A1 | 5/2009 | Shemo | |
| 2009/0141216 A1 | 6/2009 | Marrucci | |
| 2009/0201572 A1 * | 8/2009 | Yonak | G02B 1/00 359/316 |
| 2009/0256977 A1 | 10/2009 | Haddock | |
| 2009/0257106 A1 | 10/2009 | Tan | |
| 2009/0264707 A1 | 10/2009 | Hendricks | |
| 2010/0066929 A1 | 3/2010 | Shemo | |
| 2011/0069377 A1 * | 3/2011 | Wu | G02B 1/007 359/356 |
| 2011/0075073 A1 | 3/2011 | Oiwa | |
| 2011/0085117 A1 | 4/2011 | Moon et al. | |
| 2011/0097557 A1 | 4/2011 | May | |
| 2011/0109874 A1 | 5/2011 | Piers | |
| 2011/0135850 A1 | 6/2011 | Saha | |
| 2011/0188120 A1 * | 8/2011 | Tabirian | G02B 27/44 359/573 |
| 2011/0234944 A1 | 9/2011 | Powers | |
| 2011/0262844 A1 | 10/2011 | Tabirian | |
| 2012/0140167 A1 | 6/2012 | Blum | |
| 2012/0162433 A1 | 6/2012 | Fuentes Gonzalez | |
| 2012/0188467 A1 | 7/2012 | Escuti | |
| 2013/0057814 A1 | 3/2013 | Prushinskiy et al. | |
| 2013/0202246 A1 | 8/2013 | Meade | |
| 2014/0055740 A1 | 2/2014 | Spaulding | |
| 2014/0211145 A1 | 7/2014 | Tabirian | |
| 2014/0252666 A1 | 9/2014 | Tabirian | |
| 2015/0049487 A1 | 2/2015 | Connor | |
| 2015/0081016 A1 * | 3/2015 | De Sio | G02C 7/04 623/6.22 |
| 2015/0276997 A1 | 10/2015 | Tabirian et al. | |
| 2016/0023993 A1 | 1/2016 | Tabirian | |

(56) References Cited

U.S. PATENT DOCUMENTS

| | | |
|---|---|---|
| 2016/0047955 A1 | 2/2016 | Tabirian et al. |
| 2016/0047956 A1 | 2/2016 | Tabirian et al. |
| 2016/0363783 A1 | 12/2016 | Blum |
| 2017/0010397 A1 | 1/2017 | Tabirian et al. |

FOREIGN PATENT DOCUMENTS

| | | |
|---|---|---|
| GB | 2209751 | 5/1989 |
| JP | 2001142033 | 5/2001 |
| JP | 2004226752 | 8/2004 |
| WO | 2008130555 | 10/2008 |
| WO | 2008130559 | 10/2008 |

OTHER PUBLICATIONS

Tabirian, et al., PCT Application No. PCT/US15/26186 filed Apr. 16, 2015, Notification of Transmittal of the International Search Report and the Written Opinion of the International Searching Authority dated Jul. 14, 2015, 17 pages.
Report and the Written Opinion of the International Searching Authority, or the Declaration dated Oct. 10, 2016, 16 pages.
Marrucci, et al., Pancharatnam-Berry phase optical elements for wave front shaping in the visible domain, Appl. Phys. Lett. 88, 2006, 3 pages.
Early, J. et al., Twenty Meter Space Telescope Based on Diffractive Fresnel Lens, SPIE, U.S. Department of Energy, Lawrence Livermore National Laboratory, Jun. 2003, 13 pages.
Martinez-Cuenca, et al., Reconfigurable Shack-Hartmann Sensor Without Moving Elements,Optical Society of America, vol. 35, No. 9, May 2010, 3 pages.
Serak, S., et al., High-efficiency 1.5 mm Thick Optical Axis Grating and its Use for Laser Beam Combining, Optical Society of America, vol. 32, No., Jan. 2007, 4 pages.
Ono et al., Effects of phase shift between two photoalignment substances on diffration properties in liquid crystalline grating cells, Appl. Opt. vol. 48, Jan. 2009, 7 pgs.
Naydenova et al., "Diffraction form polarization holographic gratings with surface relief in side chain azobenzene polyesters" J. Opt. Soc. Am. B, vol. 15, (1998), 14 pages.
Oh et al., Achromatic polarization gratings as highly efficent thin-film polarizing beamsplitters for broadband light Proc. SPIE vol. 6682, (2007), 4 pages.
Nersisyan, S., et al., Polarization insensitive imaging through polarization gratins, Optics Express, vol. 17, No. 3, Feb. 2, 2009, 14 pages.
OISE, Optics in the Southeast, Technical Conference and Tabletop Exhibit, Optical Society of America, Orlando, FL., Nov. 12-13, 2003, 9 pages.
Dierking, Polymer Network-Stabilized Liquid Crystals, Advanced Materials, vol. 12, No. 3, 2000, 15 pages.
Tabiryan, et al., Broadband waveplate lenses, Optics Express 7091, vol. 24, No. 7, Mar. 24, 2016, 12 pages.
Tabiryan, et al. Thin waveplate lenses of switchable focal length—new generation in optics, Optics Express 25783, vol. 23, No. 20, Sep. 19, 2015, 12 pages.
Tabiryan, et al. Superlens in the skies: liquid-crystal-polymer technology for telescopes, Newsroom, 2016, 2 pages.
Nersisyan, et al., The principles of laser beam control with polarization gratings introduced as diffractive waveplates, Proc. of SPIE, vol. 7775, 2010, 10 pages.
Heller, A Giant Leap for Space Telescopes, Foldable Optics, S&TR, Mar. 2003, 7 pages.
Beam Engineering for Advanced Measurements Co., PCT Application No. PCT/US2015026186, The Extended European Search Report, filed on Mar. 8, 2017, 13 pages.
Blinov, et al., Electrooptic Effects in Liquid Crystal MAterials, Springer-Verlag New York, 1994, 17 pages.
Crawford, et al., Liquid Crystals in Complex Geometries; Formed by Polymer and Porous Networks, Taylor and Francis, 1996, 4 pages.
Honma, et al., Liquid-Crystal Fresnel Zone Plate Fabricated by Microoubbing, Japanese Journal of Applied Phsyics, vol. 44, No. 1A, 2005, 4 pages.
Tabirian, N., et al., U.S. Appl. No. 61/757,259, filed Jan. 28, 2013, 29 pages.
Beam Engineering for Advaced Measurements Co., et al., PCT Application No. PCT/US2016/038666 filed Jun. 22, 2016, Notification of Transmittal of the International Search.
Tabiryan, et al., The Promise of Diffractive Waveplates, OPN Optics and Photonics News, Mar. 2010, 6 pages.
Tabiryan, et al., Fabricating Vector Vortex Waveplates for Coronagraphy, 2012, 12 pages.
Nersisyan, et al., Study of azo dye surface command photoalignment material for photonics applications, Applied Optics, vol. 49, No. 10, Apr. 1, 2010, 8 pages.
Nersisyan, et al., Characterization of optically imprinted polarization gratings, Applied Optics, vol. 48, No. 21, Jul. 20, 2009, 6 pages.
Nersisyan, et al., Fabrication of Liquid Crystal Polymer Axial Waveplates for UV-IR Wavelengths, Optics Express, vol. 17, No. 14, Jul. 2009, 9 pages.
Nersisyan, et al., Optical Axis Gratings in Liquid Crystals and Their Use for Polarization Insensitive Optical Switching, Journal of Nonlinear Optical Physics & Materials, vol. 18, No. 1, 2009, 47 pages.
Nersisyan, et al., Polarization insensitive imaging through polarization gratings, Optics Express, vol. 17, No. 3, Feb. 2, 2009, 14 pages.
Sarkissian, et al., Longitudinally modulated nematic bandgap structure, Optical Society of America, vol. 23, No. 8, Aug. 2008, 6 pages.
Sarkissian, et al., Polarization-universal bandgap in periodically twisted nematics, Optics Letters, vol. 31, No. 11, Jun. 1, 2006, abstract, 4 pages.
Sarkissian, et al., Periodically Aligned Liquid Crystal: Potential Application for Projection Displays, Mol. Cryst. Liq. Cryst., vol. 451, 2006, 19 pages.
Sarkissian, et al., Potential application of Periodically Aligned Liquid Crystal cell for projection displays, JThE12, 2005, 3 pages.
Sarkissian, et al., Polarization-Controlled Switching Between Diffraction Orders in Transverse-Periodically Aligned Nematic Liquid Crystals, Optics Letters, Aug. 2006, abstract, 4 pages.
Schadt, et al., Photo-Induced Alignment and Patterning of Hybrid Liquid Crystalline Polymer Films on Single Substrates, Jpn. J. Appl. Phys., vol. 34, Part 2, No. 6B, Jun. 15, 1995, 4 pages.
Schadt , et al., Photo-Generation of Linearly Polymerized Liquid Crystal Aligning Layers Comprising Novel, Integrated Optically Patterned Retarders and Color Filters, Jpn. J. Appl. Phys., vol. 34, Part 1, No. 6A, Jun. 1995, 10 pages.
Schadt, et al., Optical patterning of multi-domain liquid-crystal displays with wide viewing angles, Nature, vol. 381, May 16, 1996, 4 pages.
Escuti, et al., A Polarization-Independent Liquid Crystal Saptial-Light-Modulator, Liquid Crystals X, Proc. of SPIE, vol. 6332, 2006, 9 pages.
Escuti, et al., Polarization-Independent LC Microdisplays Using Liquid Crystal Polarization Gratings: A Viable Solution (?), Dept of Electrical & Computer Engineering @ ILCC, Jul. 1, 2008, 30 pages.
Escuti, et al., Simplified Spectropolarimetry Using Reactive Mesogen Polarization Gratings, Imaging Spectrometry XI, Proc. of SPIE, vol. 6302, 2006, 11 pages.
Gibbons, et al., Surface-mediated alignment of nematic liquid crystals with polarized laser light, Nature, vol. 351, May 2, 1991, 1 page.
Gibbons, et al., Optically Controlled Alignment of Liquid Crystals: Devices and Applications, Molecular Crystals and Liquid Crystals, vol. 251, 1994, 19 pages.
Gibbons, et al., Optically generated liquid crystal gratings, Appl. Phys. Lett., 65, Nov. 14, 1994, 3 pages.
University of Central Florida, School of Optics CREOL PPCE, Optics in the Southeast, Technical Conference and Tabletop Exhibit, Nov. 12-13, 2003, 9 pages.

(56) References Cited

OTHER PUBLICATIONS

Ichimura, et al., Surface assisted photoalignment control of lyotropic liquid crystals, Part 1, Characterization and photo alignment of aqueous solutions of a water soluble dyes as lyotropic liquid crystals, J. Materials. Chem., vol. 12, 2002, abstract, 2 pages.
Ichimura, et al., Reversible Change in Alignment Mode of Nematic Liquid Crystals Regulated Photochemically by "Command Surfaces" Modified with an Azobenzene Monolayer, American Chemical Society, Langmuir, vol. 4, No. 5, 1988, 3 pages.
Zel'dovich, et al., Devices for displaying visual information, Disclosure, School of Optics/CREOL, University of Central Florida, Jul. 2000, 10 pages.
Provenzano, et al., Highly efficient liquid crystal based diffraction grating induced by polarization holograms at the aligning surfaces, Applied Physics Letter 89, 2006, 4 pages.
Titus, et al., Efficient polarization-independent, re ective liquid crystal phase grating, Applied Physics Letter 71, Oct. 20, 1197, 3 pages.
Chen, et al. An Electrooptically Controlled Liquid-Crystal Diffraction Grating, Applied Physics Letter 67, Oct. 30, 1995, 4 pages.
Kim, et al., Unusual Characteristics of Diffraction Gratings in a Liquid Crystal Cell, Advanced Materials, vol. 14, No. 13-14, Jul. 4, 2002, 7 pages.
Pan, et al., Surface Topography and Alignment Effects in UV-Modified Polyimide Films with Micron Size Patterns, Chinese Journal of Physics, vol. 41, No. 2, Apr. 2003, 8 pages.
Fuh, et al., Dynamic studies of holographic gratings in dye-doped liquid-crystal films, Optics Letter, vol. 26, No. 22, Nov. 15, 2001, 3 pages.
Yu, et al., Polarization Grating of Photoaligned Liquid Crystals with Oppositely Twisted Domain Structures, Molecular Crystals Liquid Crystals, vol. 433, 2005, 7 pages.
Crawford, et al., Liquid-crystal diffraction gratings using polarization holography alignment techniques, Journal of Applied Physics 98, 2005, 10 pages.
Seiberle, et al., 38.1 Invited Paper: Photo-Aligned Anisotropic Optical Thin Films, SID 03 Digest, 2003, 4 pages.
Wen, et al., Nematic liquid-crystal polarization gratings by modification of surface alignment, Applied Optics, vol. 41, No. 7, Mar. 1, 2002, 5 pages.
Anagnostis, et al., Replication produces holographic optics in volume, Laser Focus World, vol. 36, Issue 3, Mar. 1, 2000, 6 pages.
Gale, Replicated Diffractive Optics and Micro-Optics, Optics and Photonics News, Aug. 2003, 6 pages.
Mceldowney, et al., Creating vortex retarders using photoaligned LC polymers, Optics Letter, vol. 33, No. 2, Jan. 15, 2008, 3 pages.
Stalder, et al., Lineraly polarized light with axial symmetry generated by liquid-crystal polarization converters, Optics Letters vol. 21, No., 1996, 3 pages.
Kakichashvili, et al., Method for phase polarization recording of holograms, Sov. J. Quantum. Electron, vol. 4, No. 6, Dec. 1974, 5 pages.
Todorov, et al., High-Sensitivity Material With Reversible Photo-Induced Anisotropy, Optics Communications, vol. 47, No. 2, Aug. 15, 1983, 4 pages.
Attia, et al., Anisoptropic Gratings Recorded From Two Circularly Polarized Coherent Waves, Optics Communications, vol. 47, No. 2, Aug. 15, 1983, 6 pages.
Cipparrone, et al., Permanent polarization gratings in photosensitive langmuir blodget films, Applied Physics Letter, vol. 77, No. 14, Oct. 2, 2000, 4 pages.
Nikolova, et al., Diffraction Efficiency and Selectivity of Polarization Holographic Recording, Optica Acta: International Journal of Optics, vol. 31, No. 5, 1984, 11 pages.
Lee et al., "Generation of pretilt angles of liquid crystals on cinnamte-based photoalignment . . . ", Opt., Expr., vol. 17 (26) (Dec. 2009), abstract, 4 pages.
Yaroshchuk et al. "Azodyes as photoalignment agents for polymerizable liquid crystals", IDW'06 Digest vol. 1-3, 2006, 4 pages.
Chigrinov et al. "Anchoring properties of photoaligned azo-dye materials" Phys. Rev., E vol. 68, (Dec. 2003), 5 pages.
Pagliusi et al. Surface-induced photorefractivity in twistable nematics: toward the all-optical control of gain, Opt. Expr. vol. 16, Oct. 2008, 9 pages.
M. Honma, T. Nose, Polarization-independent liquid crystal grating fabricated by microrubbing process, Jpn. J. Appl. Phys., Part 1, vol. 42, 2003, 3 pages.
Anderson, G., et al., Broadband Antihole Photon Sieve Telescope, Applied Optics, vol. 16, No. 18., Jun. 2007, 3 pages.
Pepper, M. et al, Nonlinear Optical Phase Conjugation, IEEE, Sep. 1991, pp. 21-34, 14 pages.
Tabirian, N., Utility U.S. Appl. No. 14/194,808, filed Mar. 2, 2014, Office Action Summary dated Feb. 9, 2018, 10 pages.
Tabirian, N., Utility U.S. Appl. No. 14/324,126, filed Jul. 4, 2014, Office Action Summary dated Feb. 8, 2018, 13 pages.
Tabirian, et al., U.S. Appl. No. 14/688,197, filed Apr. 16, 2015, Office Action Summary dated Aug. 6, 2018, 19 pages.
Tabirian, et al., U.S. Appl. No. 15/621,553, filed Jun. 13, 2017, Office Action Summary dated Aug. 7, 2018, 11 pages.

\* cited by examiner

DIFFRACTIVE WAVEPLATE LENSES FOR CORRECTING ABERRATIONS AND POLARIZATION-INDEPENDENT FUNCTIONALITY

CROSS REFERENCE TO RELATED APPLICATIONS

This application claims the benefit of priority to U.S. Provisional Application Ser. No. 61/980,062 filed Apr. 16, 2014, the entire application of which is incorporated by reference in its' entirety, and this application is a Continuation-In-Part of U.S. patent application Ser. No. 13/916,627 filed Jun. 13, 2013, now Abandoned, which is a Continuation of U.S. patent application Ser. No. 12/697,083 filed Jan. 29, 2010, now Abandoned.

GOVERNMENT LICENSE RIGHTS

This invention was made with government support under Army Contract No. W911QY-12-C-0016. The government has certain rights in this invention.

FIELD OF THE INVENTION

This invention relates to optical lenses, and in particular to lenses, systems, devices, and methods of manufacturing and fabricating lenses, applications of the lenses, and combinations of said lenses, useful for imaging optics and systems, astronomy, displays, polarizers, optical communication and other areas of laser and photonics technology.

BACKGROUND OF THE INVENTION

The present invention is in the technical field of optics. More particularly, the present invention is in the technical field of lenses. Lenses are commonly made by shaping an optical material such as glass. The weight of such lenses increases strongly with diameter making them expensive and prohibitively heavy for applications requiring large area. Also the quality of a lens typically decreases with increasing size. To achieve desired features such as high-quality imaging, conventional lenses sometimes have curved surfaces that are non-spherical. The need to grind and polish conventional lenses with non-spherical surfaces can make such lenses extremely expensive. Segmented lenses such as Fresnel lenses are relatively thin, however, the structural discontinuities result in severe aberrations. Uses of holographic lenses are limited by the compromise of efficiency, spectral bandwidth and dispersion. Thus, there is a need for lenses that could be obtained in the form of thin film structurally continuous coatings on a variety of substrates.

Thus, the need exists for solutions to the above problems with the prior art.

BRIEF SUMMARY OF THE INVENTION

The objective of the present invention is providing a thin film structure that provides the ability to correct aberrations including, but not limited to, spherical aberration.

The second objective of the present invention is providing a combination of thin film lenses of continuous structure that focus electromagnetic radiation of any polarization to the same point in space, for a spherically symmetric lens; or to the same line segment in space, for a cylindrically symmetric lens.

The third objective of the present invention is providing an imaging system consisting of one or more thin film lenses with spherically or cylindrically symmetric continuous structure, in combination with a birefringent lens, thus allowing electromagnetic radiation of any polarization to be focused to the same point in space, for a spherically symmetric structure; or to the same line segment in space, for a cylindrically symmetric structure.

The fourth objective of the present invention is providing a combination of lenses with spherically or cylindrically symmetric continuous thin film structure that provides equal focal length for electromagnetic radiation of any polarization.

The fifth objective of the present invention is providing a combination of lenses with spherically or cylindrically symmetric continuous thin film structure that has the capability to correct the chromatic aberrations of a conventional imaging system employing one or more refractive lenses.

The sixth objective of the present invention is providing a combination of lenses with spherically or cylindrically symmetric continuous thin film structure that has the capability to simultaneous correct both the spherical and chromatic aberrations of a conventional imaging system employing one or more refractive lenses.

The seventh objective of the present invention is providing a flat mirror coated with a continuous thin film structure that focuses light with corrected aberrations.

Many of the exemplary applications have been described herein with terms such as "light" being used to describe the electromagnetic radiation that is acted upon by the disclosed diffractive waveplate lenses. The term "light" in this context should not be taken to restrict the scope of the disclosed embodiments to only those in which the electromagnetic radiation acted upon or manipulated by the diffractive waveplate lenses is in the visible region of the spectrum. As will be evident to those skilled in the art, the exemplary embodiments disclosed here, in addition to being applicable in the visible region of the spectrum, are equally applicable to the microwave, infrared, ultraviolet, and X-ray regions of the spectrum. Exceptions to this generalization are the applications relating to human vision, for which operation in the visible region of the spectrum is required.

The design and function of the optical lenses of the present invention have not been suggested, anticipated or rendered obvious by any of the prior art references.

Further objects and advantages of this invention will be apparent from the following detailed description of the presently preferred embodiments which are illustrated schematically in the accompanying drawings.

DETAILED DESCRIPTION OF THE INVENTION

Figure 1A:
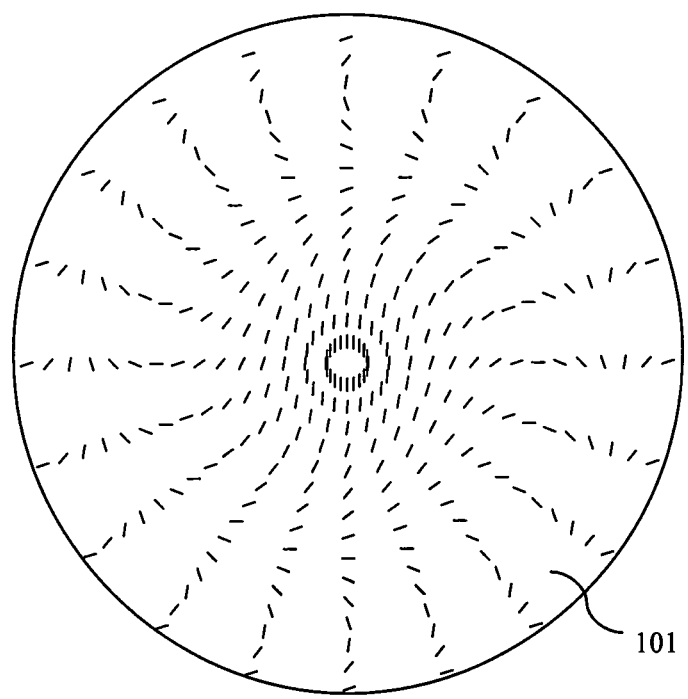
FIG. 1A shows spatial distribution of optical axis orientation in spherical diffractive waveplate lenses of one sign.

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation. In the Summary above and in the Detailed Description of Preferred Embodiments and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

In this section, some embodiments of the invention will be described more fully with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art. Like numbers refer to like elements throughout, and prime notation is used to indicate similar elements in alternative embodiments. A list of components will now be described.

101 left hand thin film
102 right hand thin film
201 continuous lines
300 plane
301 observer
302 observer
400 component/element
410 right-hand circular polarized (RHCP) light beam
411 defocused RHCP light beam
412 focused RHCP light beam
420 left-hand circular polarized (LHCP) light beam
421 defocused (LHCP) light beam
422 focused LHCP beam
430 DWL layer
440 substrate
601 collimated lens
602 lens
603 focal region
612 aspheric lens
613 focal region
614 diffractive waveplate lens
615 diffractive waveplate lens
616 diffractive waveplate lens
617 incoming beam
618 conventional lens
619 diffractive waveplate lens
701 collimated beam
702 axis
703 right-hand circular polarized beam
704 left-hand circular polarized beam
711 diffractive waveplate lens
712 diffractive waveplate lens
721 focal region
801 DWL
802 DWL
803 DWL
804 cone of light
805 focal point
901 collimated beam
902 axis
903 spherical lens
904 RHCP component
905 LHCP component
906 focal point
907 RHCP component of blue light
908 LHCP component of blue light
909 focal point
1001 diffractive waveplate lens
1002 diffractive waveplate lens
1003 diffractive waveplate lens
1010 focal point
1101 collimated light beam
1102 diffractive waveplate lens
1103 quarter waveplate
1105 focused beam

Glossary of Terms

Diffractive waveplate (DWs): A birefringent film with anisotropy axis orientation modulated in the plane of the film. Different modulation patterns are possible resulting in different optical functionality, including lens, prism, axicon, etc. Generally, DWs may possess more than one layer, and the anisotropy axis may be modulated also in the bulk of the layer.

Diffractive waveplate lens: A diffractive waveplate with lens function. It may provide spherical, cylindrical, and other types of lens action.

Optical substrate or optical film: A transparent material providing mechanical support for DWs. It may be glass, quartz, plastic, or any other material that is at least partially transparent for the wavelengths of light that propagate through the DWs. It may possess anti-reflective or anti-scratch functions.

Switchable Diffractive waveplate: A DW that can be switched between diffractive and non-diffractive states upon application of external influences such as electric fields, temperature, optical radiation, etc. Generally, the switching can take place through gradual change of diffraction spectrum.

Variable phase retarder or polarization controller: An optical component capable of controlling the polarization of light propagated through it by applying electric fields, changing temperature, exposure to a light beam, etc. Particularly, it may be a liquid crystal sandwiched between substrates coated with transparent electrodes.

Before explaining the disclosed preferred embodiments of the present invention in detail it is to be understood that the invention is not limited in its application to the details of the particular arrangements shown since the invention is capable of other embodiments. Also, the terminology used herein is for the purpose of description and not limitation.

In the description here of the invention, the term "light" will often be used to describe the electromagnetic radiation that interacts with the diffractive waveplate lenses that are the subject of this invention. Although "light" generally means electromagnetic radiation with a wavelength in the visible region of the electromagnetic spectrum, it should be understood that the usage of the term "light" in the description is not restrictive, in the sense of limiting the design and application to diffractive waveplate lenses that operate only in the visible region of the spectrum. In general, all the designs and concepts described herein apply to operation over a wide range of the electromagnetic spectrum, including the microwave, infrared, visible, ultraviolet, and X-ray regions. While physical embodiments of diffractive waveplate lenses are at present advanced for operation in the visible region of the spectrum, the designs and applications disclosed here are applicable over all the noted regions of the electromagnetic spectrum.

The present invention relates to the design and application of diffractive waveplate lenses. The term "diffractive waveplate lens" as used herein describes a thin film of birefringent material deposited on a transparent structure, for example, a thin flat substrate of optical material such as glass. This birefringent film has the property that it retards the phase of light of one linear polarization by approximately one half wave (pi radians of optical phase) relative to the light of the other linear polarization. In diffractive waveplate lenses, the optical axis orientation depends on the transverse position on the waveplate, i.e. the position in the two coordinate axes perpendicular to the surface of the diffractive waveplate lens. In other words, the optical axis orientation is modulated in one or both of the transverse directions parallel to the surface of the substrate on which the active thin film is applied. Lensing action is due to parabolic profile of optical axis orientation modulation.

There are two general types of diffractive waveplate lenses to which the present invention applies. The first type of diffractive waveplate lens is axially symmetric and is used, for example, to focus a collimated beam of light to a point in space. The second type of diffractive waveplate lens is cylindrically symmetric and is used, for example, to focus a collimated beam of light to a line segment in space. In many examples below, an optical system of circular symmetry is used as an example, but in general, all of the conclusions apply as well to optical systems of cylindrical symmetry.

In FIG. 1A, the orientation of the anisotropy axis at each point of the birefringent thin film 101 is indicated by a short line segments. In the first type of diffractive waveplate lenses to which the present invention applies, illustrated in FIG. 1A, the orientation of the anisotropy axis of the birefringent material of the thin film layer depends only on the radial distance r from a center point. This type of spherical diffractive waveplate lens is used for applications such as focusing a collimated beam of light to a point for imaging a distant scene onto a sensor array. To perform this function, the angle α that the anisotropy axis of the birefringent material makes with the coordinate axis is given by the following equation:

$$\alpha = \pm \frac{k_0}{4f} r^2$$

where $k_0 = 2\pi/\lambda$ is the wavenumber of the light that is to be focused by the diffractive waveplate lens, $\lambda$ is the wavelength of that radiation, f is the focal length of the diffractive waveplate lens (DWL), and r is the distance to the central point.

Figure 1B:
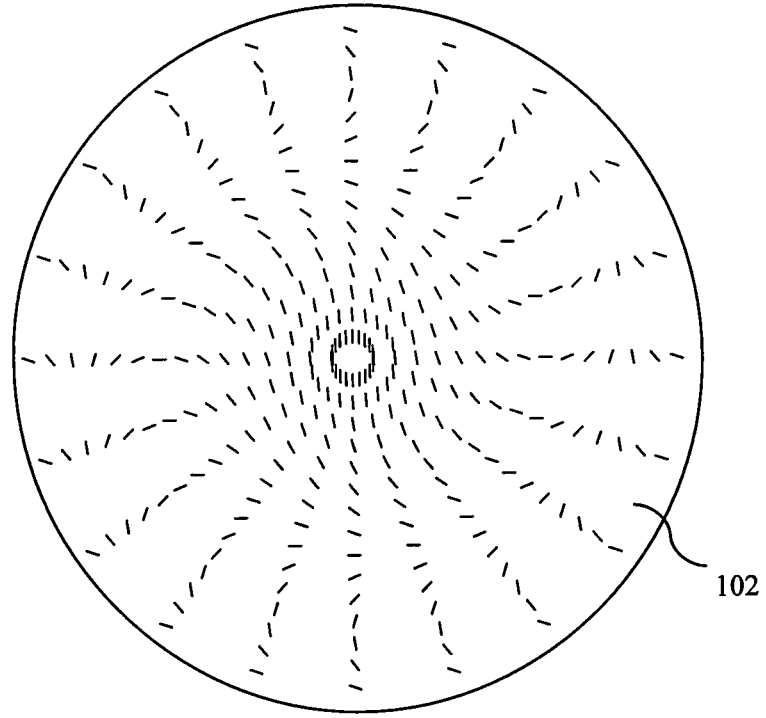
FIG. 1B shows spatial distribution of optical axis orientation in spherical diffractive waveplate lenses of an opposite sign.
Figure 2A:
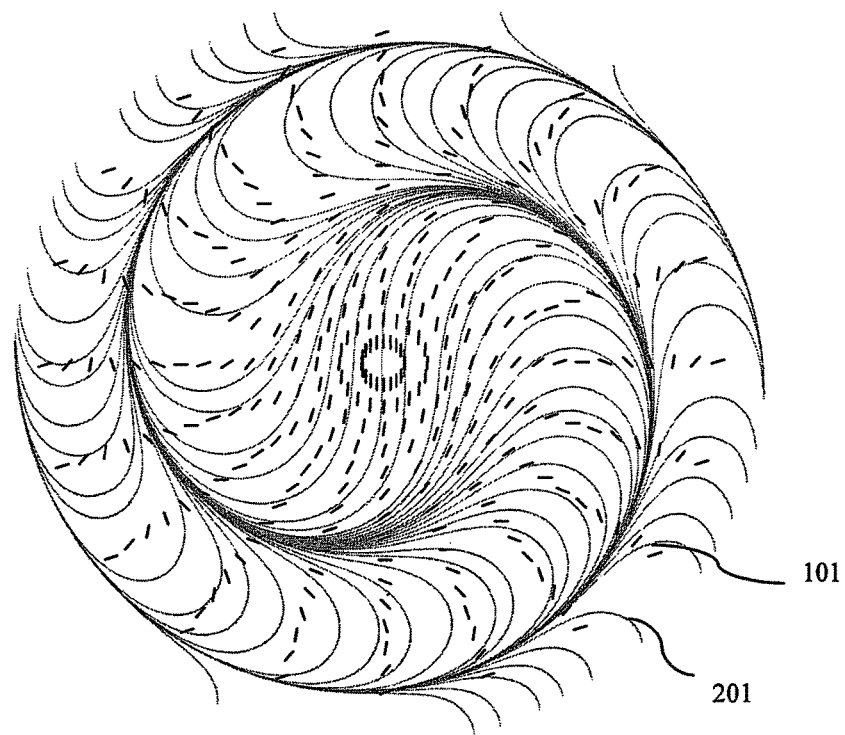
FIG. 2A shows a representation of a spherical diffractive waveplate lens with continuous alignment lines of anisotropy axis of the birefringent material.
Figure 2B:
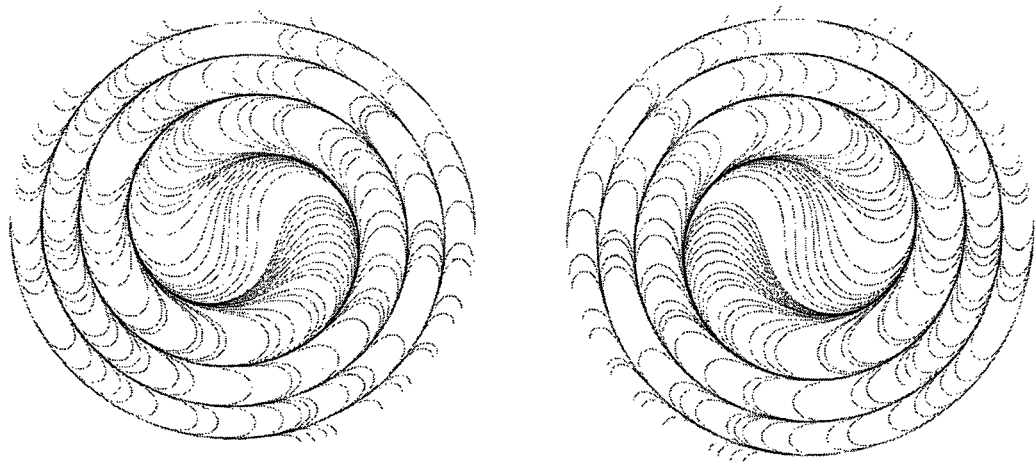
FIG. 2B shows spherical diffractive waveplate lenses of opposite signs in description with continuous alignment lines.

The difference in signs in variation of the anisotropy axis with radius designate lenses of two opposite signs. The difference in corresponding patterns 101 and 102 in FIGS. 1A and 1B, respectively, is even more visible in representation of the DWL structure by continuous lines 201 as shown in FIG. 2A. DWLs of different signs correspond to the right- and left-spiraling patterns shown in FIG. 2B.

Figure 3:
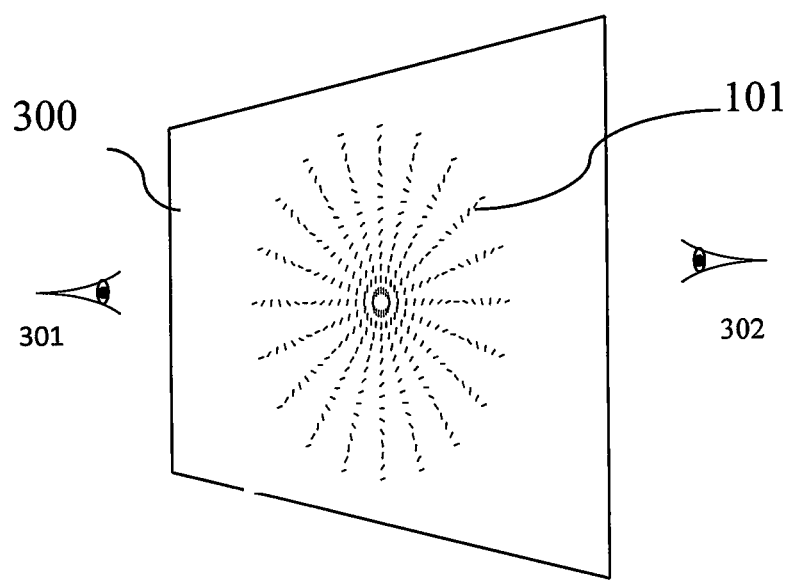
FIG. 3 shows a diffractive waveplate lense viewed from opposite sides.

In the preferred embodiment of the present invention, DWLs of opposite optical axis modulation signs need not be two separate optical components and is obtained by rotating the DWL around an axis in the plane 300 of the DWL by 180 degrees. The observers 301 and 302 looking at a given DWL from opposite sides in FIG. 3 see patterns of opposite sign.

Figure 4A:
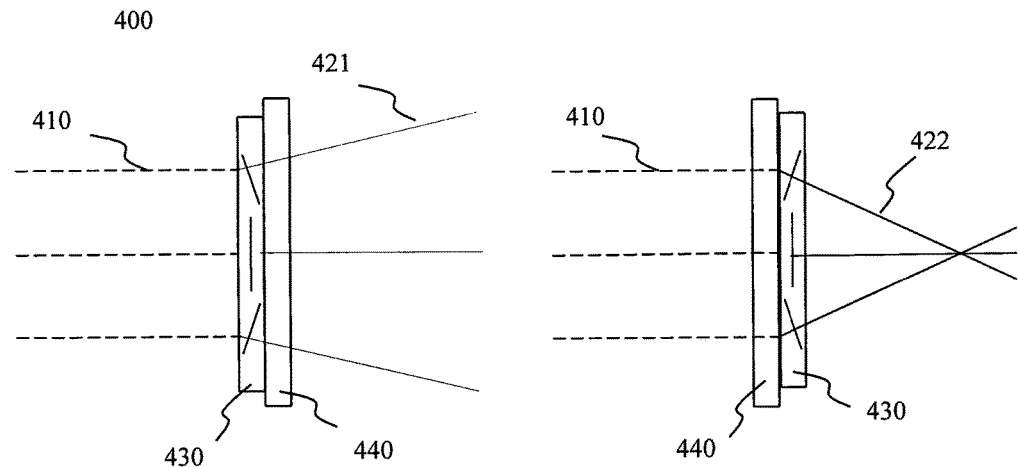
FIG. 4A shows polarization properties of focusing and defocusing of a right-hand circular polarized beam by a diffractive waveplate lens, respectively.

This optical asymmetry is described in detail in regard to FIG. 4A wherein the DWL layer 430 is shown on a substrate 440. As an example, a right-hand circular polarized (RHCP) light beam 410 is transformed into a defocused left-hand circular polarized (LHCP) beam 421 when incident from the side of the substrate. Arranging the component 400 with the substrate facing the incident RHCP beam results in a focused LHCP beam 422.

Figure 4B:
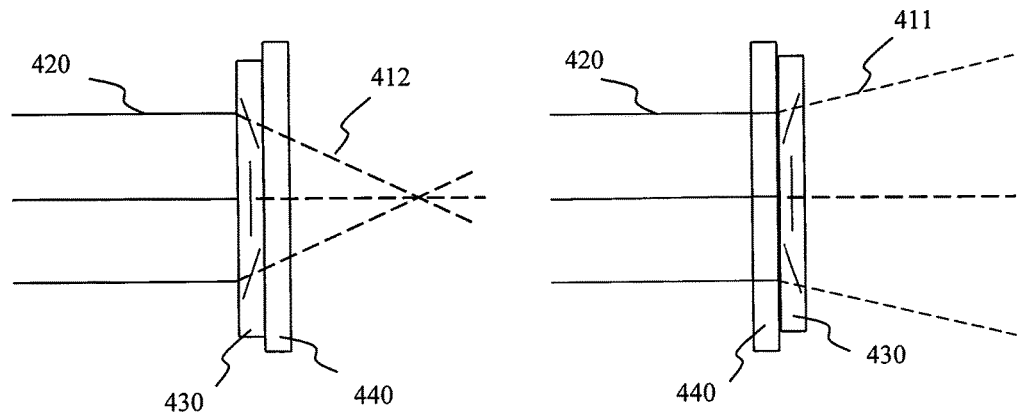
FIG. 4B shows polarization properties of focusing and defocusing a left-hand circular polarized beam by a diffractive waveplate lens, respectively.

For a LHCP light beam 420 in FIG. 4B, the situation is reversed. The LHCP beam 420 is transformed into a focused RHCP beam 412 when incident from the side of the DWL and it is transformed into defocused RHCP beam 411 when incident from the side of the substrate.

Figure 5A:
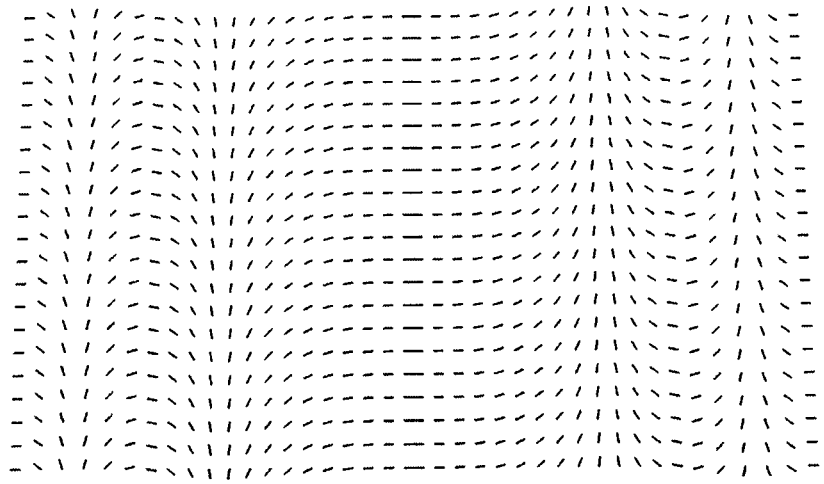
FIG. 5A shows the structure of a cylindrical diffractive waveplate lens.
Figure 5B:
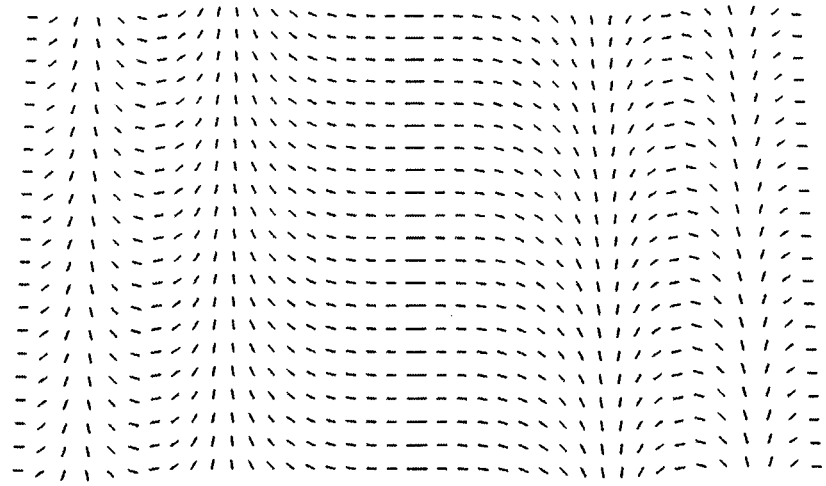
FIG. 5B shows the structure of a cylindrical diffractive waveplate lens.

In the second type of diffractive waveplate lenses to which the present invention applies, illustrated in FIGS. 5A and 5B, the orientation of the optical axis of the birefringent material of the thin film layer depends only on the linear distance x from a central axis. This type of cylindrical diffractive waveplate lens is used for applications such as focusing a beam of light to a line for imaging light from the sun onto a line of photovoltaic devices. In the paraxial approximation, the angle α that the optical axis of the birefringent material makes with the coordinate axis is given by the following equation:

$$\alpha = \pm \frac{k_0}{4f} x^2$$

where $k_0$ and f have the same meanings as before, and x is the distance from the center of the coordinate axis. FIGS. 5A and 5B correspond to patterns of different sign (cylindrical lenses of different sign).

Aspherics

Figure 6A:
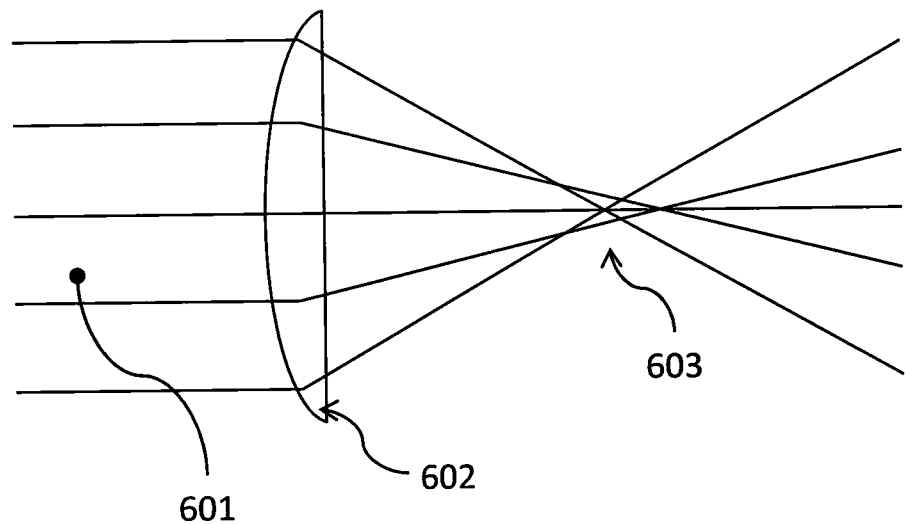
FIG. 6A shows a lens with spherical aberration focusing light to a large focal spot.
Figure 6B:
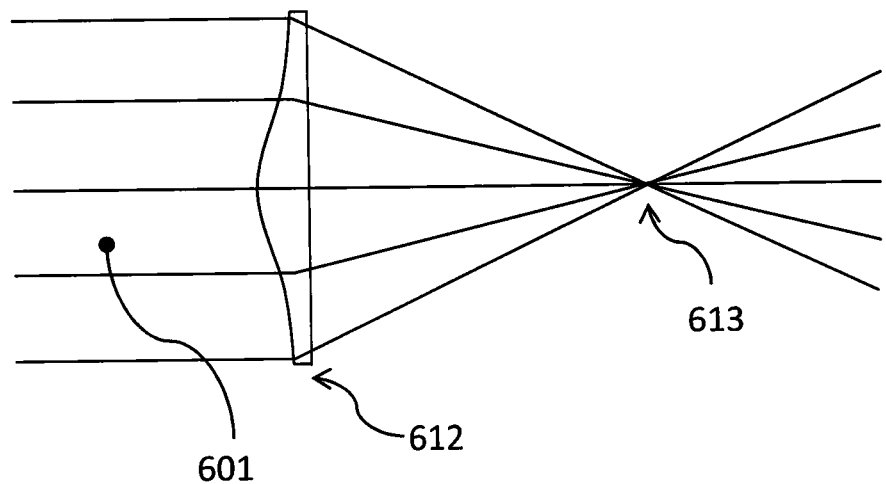
FIG. 6B shows a lens, with spherical aberration corrected, focusing light to a small focal spot.

One of the problems with conventional lenses is spherical aberration, illustrated in FIG. 6A and FIG. 6B, in which an incident collimated beam 601 is focused by a lens 602. When a refractive material such as glass formed such that one or both surfaces closely approximates a section of a sphere, such as the lens 602, then the resulting structure can be used to focus light as illustrated in FIG. 6A. However, as is well known in the art, when focused by a lens constructed in this way, the rays of light from a distant source are not all brought to the same focal point. Specifically, such a lens with spherical surfaces will bring the peripheral rays, the rays at the edge of the beam, to a focus closer to the lens than the point to which the lens brings the rays closer to the axis. Hence, the rays in the focal region 603 in FIG. 6A do not all pass through the same point. This phenomenon is called spherical aberration.

By means of modifying one of the surfaces of a lens such that the surface is not spherical (i.e. such that the surface is aspherical), all incident light in a collimated beam can be brought to the same focal point, as indicated in FIG. 6B. With an appropriately designed aspheric lens 612, all the rays in the focal region 613 pass through the same point. However, fabrication of such aspheric lenses is often very expensive, and therefore their use is impractical for many applications.

A major advantage of diffractive waveplate lenses is that the focusing effect of aspheric surfaces of arbitrary form can be produced simply by changing the dependence of optical axis orientation of the birefringent film with coordinate, $\alpha = ax + bx^2 + cx^3 + \ldots$. For such lenses, unlike the situation with conventional lenses, the manufacturing expense of a lens that has no spherical aberration will not be significantly greater than for a lens that does have spherical aberration.

Figure 6C:
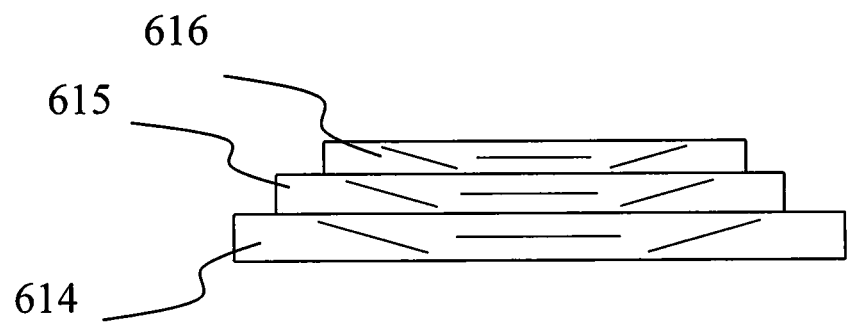
FIG. 6C shows a multilayer system of diffractive waveplate lenses of varying spatial frequency of optical axis orientation and different area.

Another preferred embodiment of current invention for obtaining nonlinear orientation modulation pattern comprises stacking layers of diffractive waveplate lenses with varying modulation patterns and varying degree of overlap. A system of three such layers, 614, 615, and 616 is shown in FIG. 6C.

Correcting Aberrations of Conventional Lenses

Figure 6D:
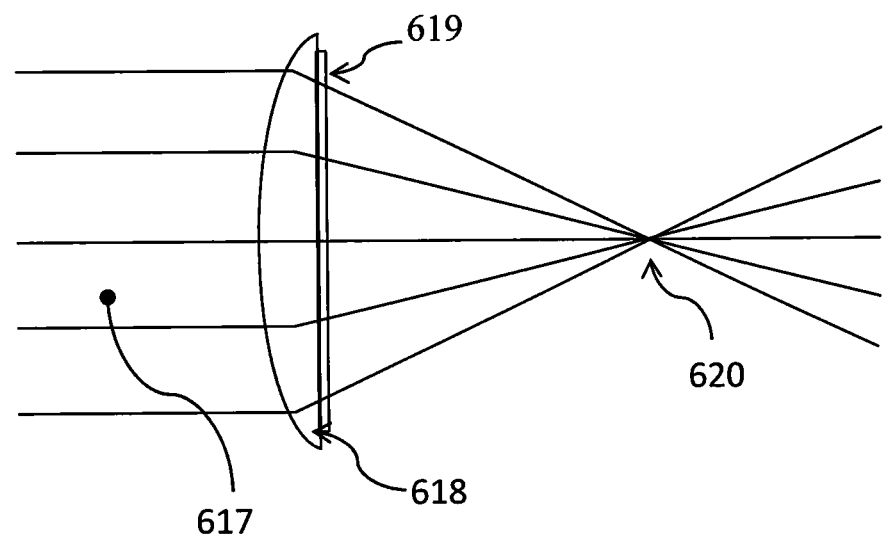
FIG. 6D shows a lens with aberrations corrected with a diffractive waveplate coating.

In one of the embodiments of the current invention shown in FIG. 6D, the thin film diffractive waveplate lens 619 may be deposited on a conventional lens 618 to correct for aberrations and focus an incoming beam 617 onto the same point in space 620.

Polarization-Independent Focusing

In general, the optical deflection angle resulting from a light beam propagating through a diffractive waveplate lens depends on the circular polarization of the light. As a result, if the focal length of a lens such as the ones illustrated in FIG. 1 is f for right-hand-circular polarized (RHCP) light as an example, then the focal length of the same lens for left-hand-circular polarized (LHCP) light will be −f. Therefore, a diffractive waveplate lens that converges a collimated beam of RHCP light will diverge a beam of LHCP light. This is illustrated by the action of the diffractive waveplate lens 711 in FIG. 7, in which an incident collimated beam 701, centered on axis 702, and including both a RHCP component and a LHCP component, converges the RHCP component 703 and diverges the LHCP component 704 of the incident beam.

In many applications, one of the functions of the optical system is to bring light to a focal point (in the case of an axially symmetric system) or to a focal line (in the case of a cylindrically symmetric system). It is often desirable for light of all polarizations to be brought to the same focal point or focal line. In the case of diffractive waveplate lenses, for which the focal length of a single lens for LHCP light is opposite in sign to the focal length for the same lens for RHCP light, it is possible to bring light of both polarizations to the same focal point or focal line by the use of two diffractive waveplate lenses. In the preferred embodiment the focal lengths of the two lenses are related as $$|f_2| = |f_1| - \frac{d^2}{|f_1|}$$

where the distance between the two lenses d is smaller than the absolute value of the focal length of the $1^{st}$ lens, $d < |f_1|$. By that, the back focal length $f_{BFL}$ of the system of two lenses, the distance of the focal spot from the second lens, is determined by equation $$f_{BFL} = \frac{f_1^2}{d} - d$$

Figure 7:
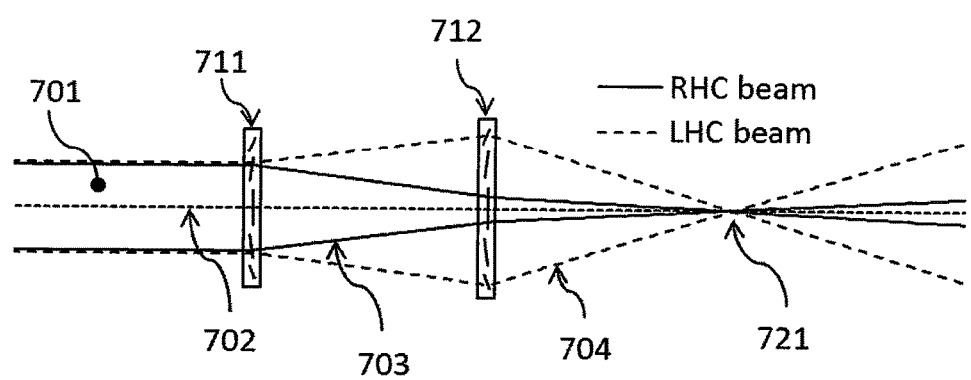
FIG. 7 shows a pair of diffractive waveplate lenses focusing light to the same spot for right hand circular (RHC) polarization as well as left hand circular (LHC) polarization.

For example, the distance between diffractive waveplate lens 711 and diffractive waveplate lens 712 can be 50 mm, the focal lengths of lenses 711 and 712 for RHCP light 703 can be 70.7 mm and −35.4 mm, respectively. Therefore, the focal lengths of lenses 711 and 712 for LHCP light 704 are −70.7 mm and 35.4 mm, respectively. As shown in FIG. 7, this combination of focal lengths and spacing results in both RHCP light 703 and LHCP light 704 being brought to the same focal point 721.

As will be evident to those skilled in the art, if an optical system brings light of both RHC polarization and LHC polarization to a single point or line focus, then it will bring light of any polarization to the same point or line focus. Therefore FIG. 7 demonstrates the ability with two diffractive waveplate lenses to bring light in any polarized or unpolarized beam to the same point or line focus.

As previously noted, for diffractive waveplate lenses of the type that is the subject of the present invention, the sign of focal length for LHC polarized light is opposite to that of the focal length for RHC polarized light. It was shown by means of FIG. 7 and the associated discussion that despite the difference in focal length for light of the two possible circular polarizations, it is possible to focus light of any polarization with a combination of two diffractive waveplate lenses. However, there may be some applications that an alternative method can be used to focus light of both polarizations, using only a single diffractive waveplate lens and an additional optical element. For example, instead of using two diffractive waveplate lenses, a single diffractive waveplate lens combined with a waveplate and a refractive lens made from a birefringent material could also be used to perform focusing of light of any polarization. Methods of combining diffractive waveplate lenses into optical systems that include such waveplates and birefringent refractive elements will be evident to anyone skilled in the art of optical design, once the fundamental characteristics of diffractive waveplate lenses of this invention are revealed.

System with Same Effective Focal Length

Figure 8:
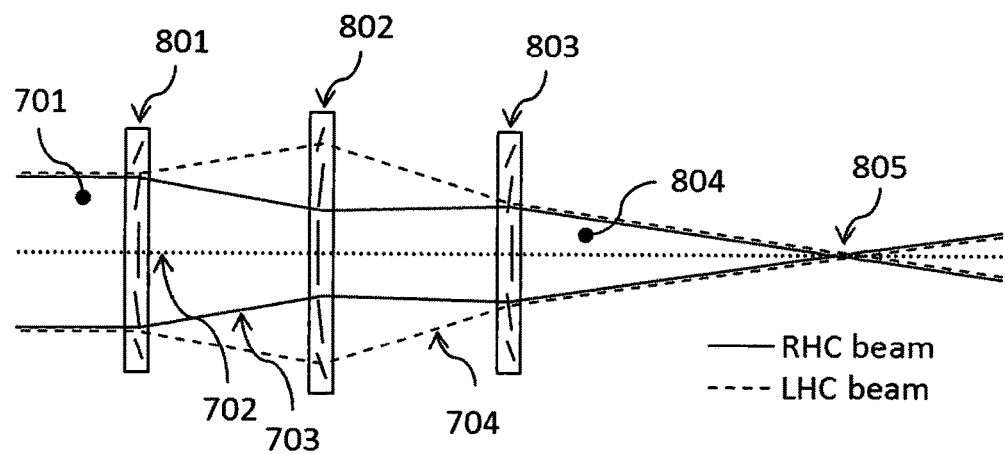
FIG. 8 shows a system of a triplet of diffractive waveplate lenses focusing light to the same spot for light of RHC polarization or LHC polarization, said system having the same effective focal length for either polarization.

As will be evident to those skilled in the art, the effective focal length (EFL) of the optical system comprising lens 711 and 712 in FIG. 7 is much different for light of RHC polarization than it is for light of LHC polarization. In some applications, it is required that light of all polarizations be focused with the same EFL. The capability of a combination of three diffractive waveplate lenses to not only bring light of any polarization to the same point or line focus, but also to have the same EFL for light of any polarization, as illustrated in FIG. 8. As in FIG. 7, in FIG. 8 an incident beam 701 symmetrically disposed about a system optical axis 702, comprising both a RHCP component 703 and a LHCP component 704, is incident on the optical system. However, in FIG. 8, the optical system now consists of three lenses 801, 802, and 803, with a spacing of 30 mm between adjacent lenses, and with focal lengths of 70.7 mm, −35.4 mm, and 45.5 mm, respectively.

As shown in FIG. 8, this combination of three diffractive waveplate lenses brings both the RHCP component 703 and the LHCP component 704 of the incident beam to the same focal point 805. While in both FIG. 7 and FIG. 8 both polarization components of the incident light beam 701 are brought to the same focal point, the significant difference between the two figures is that in FIG. 8, the cone angle of the cone of light 804 that converges to the focus 805 is the same for both the RHC polarization component 703 and the LHC polarization component 704, as must be the case if and only if the system EFL is the same for both components. FIG. 8 therefore demonstrates that with three diffractive waveplate lenses, light of any polarization can be brought to the same focal point, with the same EFL.

Correcting Chromatic Aberration

Due to the diffractive nature of diffractive waveplate lenses, the deflection angle for a given grating is a function of wavelength, in accordance with the well-known transmission grating diffraction condition, $d \sin \theta = m\lambda$. Here d is the grating spacing, $\theta$ is the angle through which the grating deflects the beam, m is the order of diffraction, and $\lambda$ is the wavelength. The phase gratings used in diffractive waveplate lenses are designed to be continuous in nature, eliminating all but the first orders of diffraction. Also, for illustrative purposes, it is useful to consider only the paraxial case, in which the angle $\theta$ through which the beam is diffracted is small compared with $\pi$, in which case $\sin \theta$ can be approximated by $\theta$. The equation above therefore becomes $d\theta \approx \lambda$. That is, in the paraxial approximation, the deflection angle of a ray of light incident on a local area of a diffractive waveplate lens is directly proportional to the wavelength of the light. As a direct consequence, the focal length of the lens is inversely proportional to wavelength.

Because of this strong dependence of the focal length of a diffractive waveplate lens on wavelength, such lenses can be used to correct for chromatic aberration in optical systems containing refractive elements. Chromatic aberration, as the expression is used here, is the dependence of the focal position on wavelength. Due to the dependence of the index of refraction n of any dielectric medium on wavelength, every imaging system that employs such media suffers from chromatic aberration.

Figure 9A:
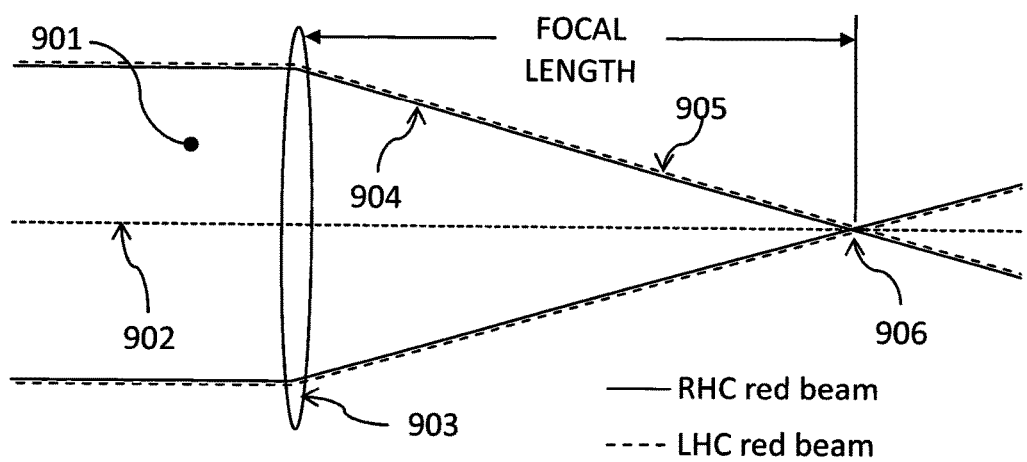
FIG. 9A shows a conventional glass lens focusing light in the red region of the spectrum to a small focal spot.

To illustrate the ability of diffractive waveplate lenses to correct for chromatic aberration, a specific example will be used. FIG. 9A illustrates an imaging system employing a single refractive element made with BK7 glass, an optical material available from Schott Advanced Optics. A collimated beam 901 of white light from a distant source is incident on spherical lens 903 with aperture centered on axis 902. Although BK7 is isotropic, and therefore does not act any differently on RHCP light than it acts on LHCP light, we will distinguish between these two components of the incident unpolarized light because (later in this discussion) diffractive waveplate lenses are considered whose effects differ between these two polarization components. With only the refractive element made from BK7 in place, both the RHCP component 904 and the LHCP component 905 of the red component of the white input beam are brought to the same focal point 906.

Figure 9B:
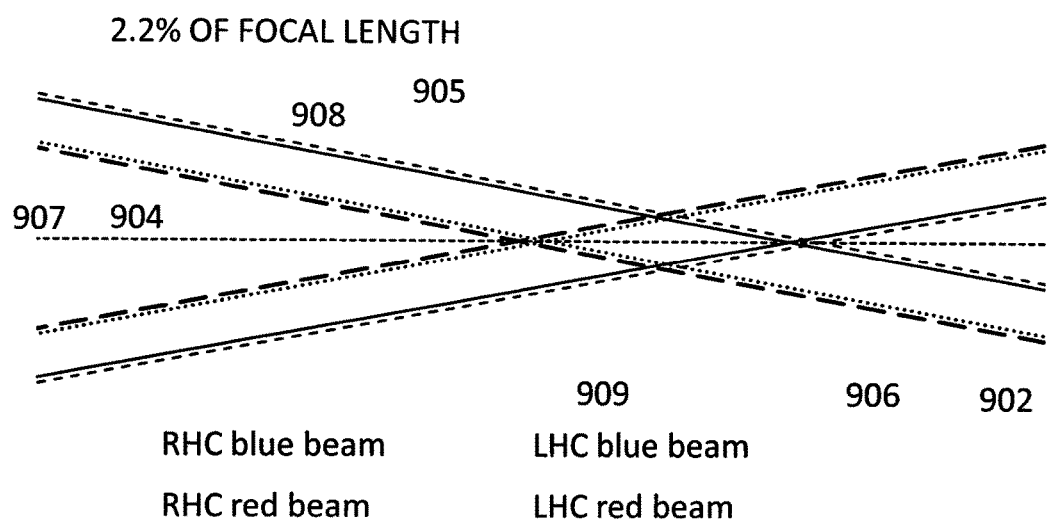
FIG. 9B shows the paths of rays of light in the red region of the spectrum, and light in the blue region of the spectrum, near the focus of a glass lens, illustrating the fact that light with different wavelengths is focused to different axial locations by the glass lens.

The BK7 material from which the refractive lens in FIG. 9A is made has an index of refraction of n=1.515 for red light (wavelength $\lambda$=650 nm) and n=1.526 for blue light (wavelength $\lambda$=450 nm). As a result, the focal length of the lens is slightly shorter for blue light than it is for red light. This is shown in FIG. 9B, showing a magnified view of the region near the focal point. The focal point 909 on the axis 902 of the input beam, for both the RHCP component of the blue light 907 and the LHCP component of the blue light 908, is 2.2% closer to the lens than the focal point 906 for the two polarization components of the red light.

For optical systems such as cameras, it is undesirable for the focal positions at any two wavelengths within the operating wavelength band to differ significantly. Therefore, chromatic aberration correction is an important part of the design of such optical systems. The most common approach to chromatic aberration correction in refractive imaging systems is to include refractive elements of multiple types, with various indices of refraction and various dependences of index of refraction on wavelength. These approaches increase the complexity and cost of the system. Therefore, there is a need for alternative approaches to chromatic aberration correction.

Figure 10A:
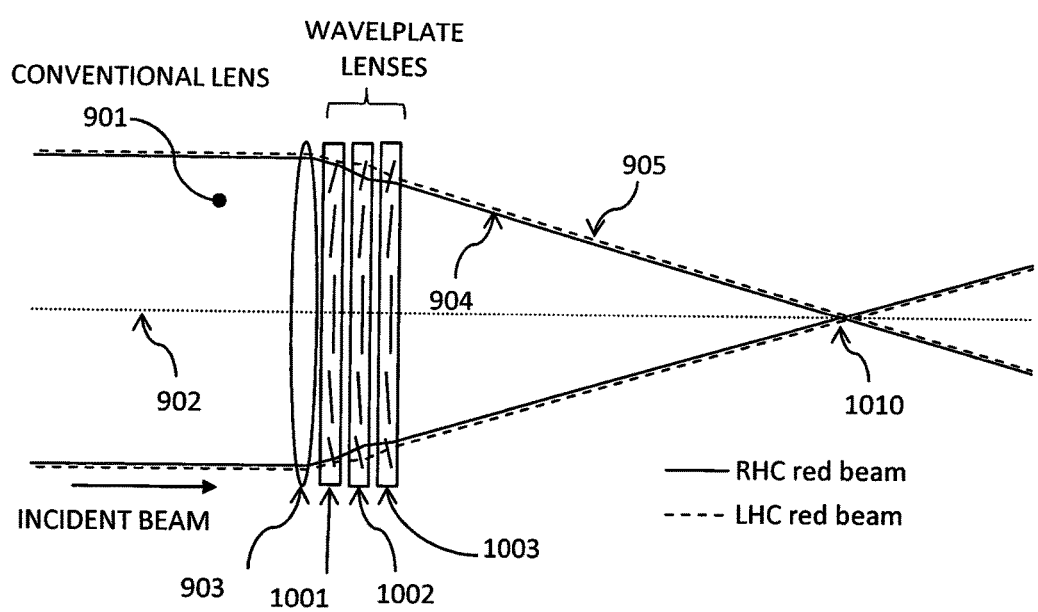
FIG. 10A shows a combination of one glass lens and three diffractive waveplate lenses focusing light in the red region of the spectrum to a small focal spot.

FIG. 10A illustrates correction of the chromatic aberration in a conventional refractive lens by employment of a set of three diffractive waveplate lenses. As was the case for FIGS. 9A and 9B, white light collimated beam 901 is incident along an axis 902 onto the conventional BK7 glass lens 903. FIG. 10A includes three diffractive waveplate lenses 1001, 1002, and 1003. As is evident from the figure, the path of red light through the combined system is slightly different for the RHCP component 904 than it is for the LHCP component 905, but both of the polarization components of the red light are brought to the same focal point 1010. The focal lengths of the lenses shown in the figure for RHCP polarized red light are 10.00 mm, 14.00 mm, −7.00 mm, and 14.07 mm for lenses 903, 1001, 1002, and 1003, respectively. As noted previously, for the diffractive waveplate lenses, the focal lengths change sign for LHC polarized light.

Figure 10B:
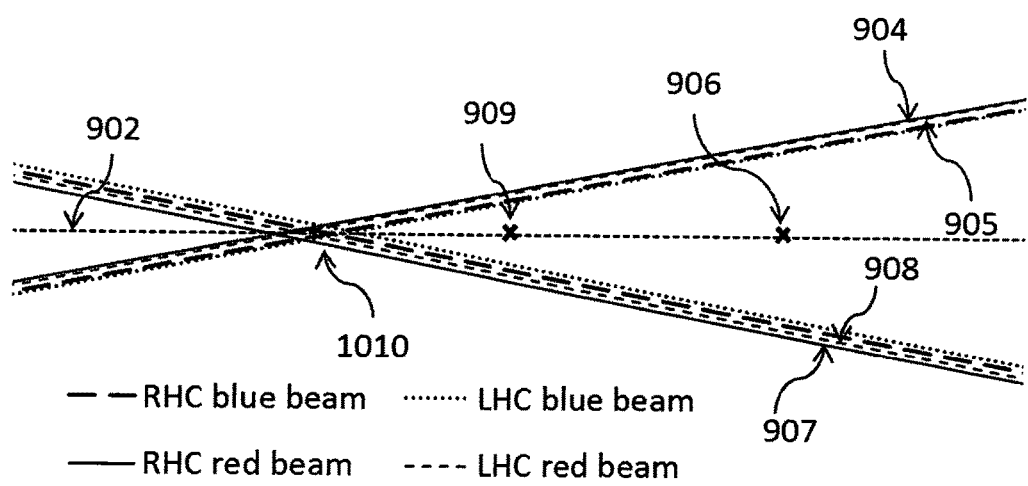
FIG. 10B shows the paths of rays of light in the red region of the spectrum, and light in the blue region of the spectrum, near the focus of the combination of one glass lens and three diffractive waveplate lenses, illustrating the fact that light with different wavelengths is focused to the same axial location by said combination of lenses.

FIG. 10B shows the ability of the lens combination illustrated in FIG. 1 OA to correct for chromatic aberration. The focal positions 906 and 909 for red and blue light, respectively, before the addition of diffractive waveplate lenses 1001, 1002, and 1003, are shown in FIG. 10B for reference. Light of all four considered polarization/wavelength combinations is brought to the same focal point 1010 after the addition of lenses 1001, 1002, and 1003. In FIG. 10B, the paths of the RHC red beam 904, LHC red beam 905, RHC blue beam 907, and LHC blue beam 908 are shown slightly offset vertically for clarity, but for the considered optical design, the four beams come to exactly the same focal point 1010.

In the discussion of FIG. 6 it was noted that by adjusting the grating spacing in a diffractive waveplate lens, spherical aberration can be eliminated. In the discussion of FIG. 10 it was demonstrated that chromatic aberration correction of a refractive imaging system is possible by the addition of appropriate diffractive waveplate lenses. Once the mechanism of correcting for spherical aberration alone, and the mechanism for correcting for chromatic aberration alone, methods will be evident to those skilled in the art that allow the use of diffractive waveplate lenses to be used to simultaneously compensate for both spherical and chromatic aberration.

Camera Lens

An example of uses of diffractive waveplate lenses of the present invention are camera lenses and machine vision wherein the contrast reduction due to presence of defocused beam does not affect required image information obtained due to focused portion of the beam.

Fiber Illuminator/Focusing System

An important use of diffractive waveplate lenses in the current invention are polarization maintaining fibers. As an example, the diffractive waveplate lens coated at the output facet of the fiber may allow collimating or focusing the light emerging from the fiber.

Partially Focused Beams

In another exemplary embodiment, waveplate lenses allow arbitrary and selectable fraction of the optical power in the beam to be deflected by the diffractive structure of the diffractive waveplate lens, and the balance of the optical power in the beam can be passed without deflection. This is accomplished by setting an optical retardation of one linear polarization relative to the other of more than zero retardation (at which no beam deflection occurs), but less than one-half wave of retardation (at which 100% of the optical power in the beam is deflected by the diffractive structure). The fraction of power focused or defocused by the lens can be adjusted to any value between 0% and 100%. For example, in a fiber coupling application, the fraction of the power transferred between fibers can be varied from 0% to nearly 100%.

Flat Focusing Mirror

Figure 11:
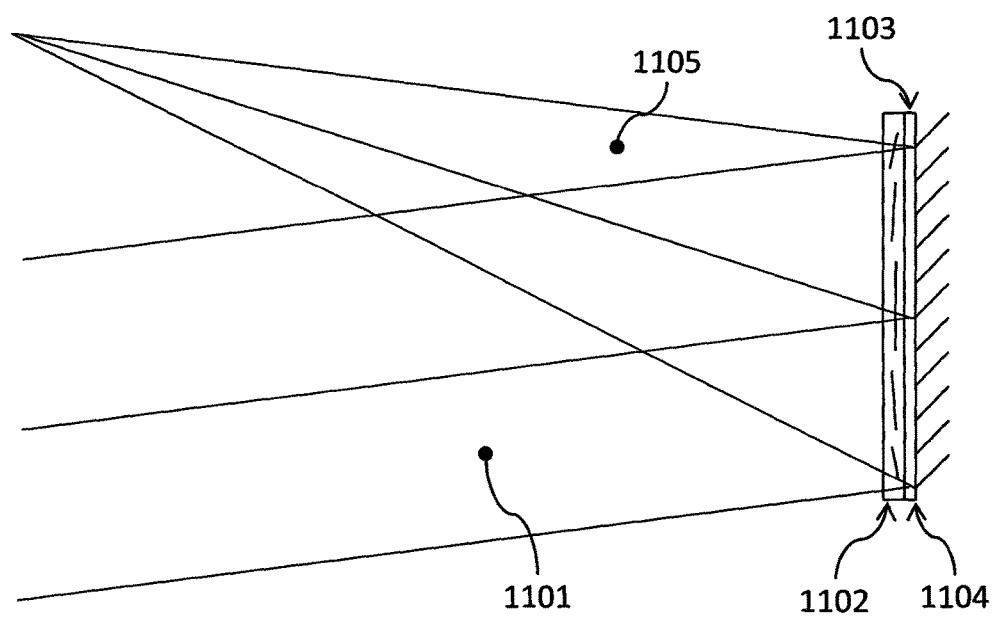
FIG. 11 shows a planar mirror converted into aberrations corrected focusing mirror by addition of the diffractive waveplate lens coating.

While all of the exemplary embodiments discussed herein are of a realization of diffractive waveplate lenses employed in a mode in which the optical beam is transmitted through the thin film diffractive waveplate lens and through the underlying substrate, an alternative embodiment is to apply the thin film diffractive waveplate lens to a flat mirror as demonstrated in FIG. 11. In this manner, flat reflective optical elements can be fabricated to have a wide variety of beam deflecting properties, including the ability to focus light with a flat reflective optical element. In one of the preferred embodiments shown in FIG. 11, a flat mirror 1104 is coated with a quarter waveplate 1103 and a diffractive waveplate lens 1102. A circular polarized collimated light beam 1101 is thus reflected from the system a focused beam 1105, for example.

The exemplary embodiments described herein have assumed either explicitly or implicitly that the thin film constituting the diffractive waveplate lens is applied to the flat surface of a solid substrate such as glass. Neither the assumption of a solid substrate, nor the assumption of a flat surface, should be taken as restrictive in defining the potential embodiments of this invention. As will be evident to anyone skilled in the art, the coatings may be applied to curved substrates, and to flexible substrates. All of the exemplary embodiments described herein could also be realized with either a curved substrate, a flexible substrate, or a substrate that is both curved and flexible.

Solar Concentrators and Telescopes

In a preferred embodiment, light-weight flat lenses and/or mirrors of the present invention may be used for solar concentrators, particularly, portable solar concentrators and for telescopes.

Microwave, Infrared, Ultraviolet, and X-Ray Regions of the Spectrum

By merely changing the thickness of the layer, in a preferred embodiment of current invention, diffractive waveplate lenses are optimized for use in different parts of the spectrum, spanning microwave and to short wavelengths.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A spherical aberration corrected diffractive waveplate lens optical film, comprising:
   an optical substrate; and
   at least one birefringent material layer deposited on said optical substrate, an optical axis orientation angle of said at least one birefringent material layer being a nonlinear function of Cartesian coordinates in a plane of said at least one birefringent material layer such that an optical radiation transmitted through said at least one birefringent material and said optical substrate is focused to one of a point in space and a line segment in space with no spherical aberrations.

2. The spherical aberration corrected diffractive waveplate lens optical film as in claim 1, wherein the at least one birefringent material layer includes at least two birefringent material layers, wherein the nonlinear function of Cartesian coordinates in the plane of said at least one birefringent material layer of the optical axis orientation angle is different for the at least two birefringent material layers allowing to control at least one of: effective focal length, spherical aberrations and spectrum of diffraction efficiency of the spherical aberration corrected diffractive waveplate lens optical film.

3. The spherical aberration corrected diffractive waveplate lens optical film as in claim 2, wherein coverage areas of the at least two birefringent material layers on said optical substrate are different allowing to control at least one of: distribution of focusing power, diffraction efficiency spectrum and aberration of the spherical aberration corrected diffractive waveplate lens optical film over an area of the spherical aberration corrected diffractive waveplate lens optical film.

4. The spherical aberration corrected diffractive waveplate lens optical film as in claim 3 wherein the at least one birefringent material layer is selected based on at least one of the nonlinear function of Cartesian coordinates in the plane of said at least one birefringent material layer of the optical axis orientation angle and sizes of said at least one birefringent material layer to provide progressively varying focusing power of said at least one birefringent material layer over said optical substrate.

5. The spherical aberration diffractive waveplate lens optical film as in claim 1 wherein full-wave phase retardation of said at least one birefringent material layer is selected to provide for no diffraction efficiency for a predetermined wavelength or range of wavelengths.

6. An optical system comprising:
two or more diffractive waveplate lenses positioned at a predetermined distances from each other, the two or more diffractive waveplate lenses including an optical substrate with at least one birefringent material layer deposited on said optical substrate, an optical axis orientation angle of said at least one birefringent material layer being a nonlinear function of Cartesian coordinates in a plane of said at least one birefringent material layer such that the optical radiation transmitted through said at least one birefringent material and said optical substrate is focused to one of a point in space and a line segment in space with no spherical aberrations.

7. The optical system of claim 6 wherein said position of the at least two diffractive waveplate lenses diffracts polarized light to a same point focus or a line focus.

8. The optical system of claim 7 wherein said position of the at least two diffractive waveplate lenses diffracts light of any polarization to the same point focus or the line focus such that an effective focal length of the optical system is the same for light of any polarization.

9. The optical system of claim 8 further comprising:
a refractive imaging system.

10. The optical system as in claim 9 wherein both a spherical and a chromatic aberration of said refractive imaging system are corrected.

11. The optical system as in claim 9 further comprising a light source.

12. The optical system as in claim 11 wherein a predetermined portion of a light power provided by said light source is focused.

13. An optical device for imaging, communication and solar concentrator applications comprising:
a flat mirror;
a quarter-wave phase retarder film deposited on said mirror; and
a diffractive waveplate lens deposited on said quarter-wave phase retarder film, the diffractive waveplate lens including an optical substrate with at least one birefringent material layer deposited on said optical substrate, an optical axis orientation angle of said at least one birefringent material layer being a nonlinear function of Cartesian coordinates in a plane of said at least one birefringent material layer such that an optical radiation transmitted through said at least one birefringent material and the optical substrate is focused to one of a point in space and a line segment in space with no spherical aberrations.

14. The optical device as in claim 13 wherein the flat mirror, the quarter-wave phase retarder film and the diffractive waveplate lens are broadband.

* * * * *